United States Patent [19]

Nowosielski et al.

[11] Patent Number: 5,605,545
[45] Date of Patent: Feb. 25, 1997

[54] TUBING SYSTEM FOR DELIVERING FLUID TO A SURGICAL SITE

[75] Inventors: Albert Nowosielski, Roselle; Robert Mantell, Arlington Heights; Peter Manzie, Berwyn; Charles Zander, Grayslake, all of Ill.

[73] Assignee: Northgate Technologies Incorporated, Elgin, Ill.

[21] Appl. No.: 238,647

[22] Filed: May 5, 1994

[51] Int. Cl.⁶ ........................................... A61M 1/00
[52] U.S. Cl. ........................ 604/118; 604/48; 604/93; 604/246
[58] Field of Search ........................ 604/19, 27–34, 604/46, 48, 49, 53, 65, 67, 93, 118, 131, 151, 246, 250, 257, 258, 280, 283, 284

[56] References Cited

U.S. PATENT DOCUMENTS

| 3,900,022 | 8/1975 | Widran . | |
|---|---|---|---|
| 4,180,074 | 12/1979 | Murry et al. . | |
| 4,391,599 | 7/1983 | Jenkins | 604/118 |
| 4,439,179 | 3/1984 | Lueders et al. | 604/34 |
| 4,604,089 | 8/1986 | Santangelo et al. . | |
| 4,613,325 | 9/1986 | Abrams | 604/65 |
| 4,650,462 | 3/1987 | DeSatnick et al. . | |
| 4,655,197 | 4/1987 | Atkinson . | |
| 4,702,733 | 10/1987 | Wright et al. . | |
| 4,713,051 | 12/1987 | Steppe et al. . | |
| 4,820,265 | 4/1989 | DeSatnick et al. . | |
| 4,874,359 | 10/1989 | White et al. | 604/4 |
| 4,883,455 | 11/1989 | Leonard | 604/4 |
| 4,940,457 | 7/1990 | Olson . | |
| 5,004,459 | 4/1991 | Peabody et al. | 604/29 |
| 5,011,469 | 4/1991 | Buckberg et al. | 604/4 |
| 5,019,038 | 5/1991 | Linden . | |
| 5,053,002 | 10/1991 | Barlow . | |
| 5,061,241 | 10/1991 | Stephens et al. | 604/114 |
| 5,098,387 | 3/1992 | Weist et al. . | |
| 5,152,746 | 10/1992 | Atkinson et al. . | |
| 5,423,749 | 6/1995 | Merte et al. | 604/67 |

FOREIGN PATENT DOCUMENTS

| 2371202 | 7/1978 | France | 604/118 |
|---|---|---|---|

*Primary Examiner*—Corrine M. McDermott
*Attorney, Agent, or Firm*—Brinks Hofer Gilson & Lione

[57] ABSTRACT

A tubing set and method for use with a system for providing pressurized fluid from a fluid source to a surgical site. The system includes a fluid source, a length of flexible tubing having one end connected to the fluid source and another end connected to a surgical instrument, and a peristaltic type pump into which a middle portion of flexible tubing is positioned so that the peristaltic type pump can pump fluid from the source to the surgical instrument by bearing on the exterior of the tubing. The improved tubing set also includes a by-pass section of tubing connected between the tubing inlet and the tubing outlet in parallel with the middle portion of the flexible tubing. The by-pass section provides pressure relief to the system so that pressure in the tubing will not build up distally of the location of the peristaltic pump.

17 Claims, 2 Drawing Sheets

TUBING SYSTEM FOR DELIVERING FLUID TO A SURGICAL SITE

BACKGROUND OF THE INVENTION

The present invention relates to a system for providing fluid to a surgical site inside the body and in particular the present invention relates to a system and method for providing a pressurized fluid for irrigating or distending an internal body site or organ that is accessed through a relatively small incision, natural orifice of the body, or in conjunction with a laparoscope, endoscope, resectoscope or similar device used to perform a surgical procedure.

Certain surgical procedures, such as urological, gynecological, and laparoscopic surgeries, are performed inside the body either through an apparatus or a very small incision or through a small natural orifice of the body. An advantage of performing surgery in these ways is that it is less traumatic to the patient and allows quicker recovery, compared to conventional open surgery. When performing these types of surgeries, it is often necessary to provide for continuous or intermittent fluid delivery to the internal surgical site. For example, in some procedures, pressurized fluid is used to distend an internal body cavity or organ to facilitate accessibility to the surgical site with laparoscopic tools. Also, it may be necessary to flush the surgical area with water or another fluid to clear the area to facilitate observation and to enable the physician to proceed.

One commonly used system for delivering fluid to an internal surgical site uses a positive displacement-type pump, such as a peristaltic pump. This common system consists of providing several plastic bags, e.g. one or three liter bags, containing a fluid, such as sterile water, on an IV pole, connecting tubing to the bags, and positioning a portion of the tubing to the peristaltic pump. The peristaltic pump is suitably sized and designed to accommodate the tubing. The tubing is connected to an appropriate surgical instrument that can be used to deliver the fluid to the internal surgical site under pressure. Examples of such surgical instruments include endoscopes, resectoscopes, irrigation-aspiration cannula, laparoscopes, and so on.

The above described procedure for delivering fluid to a surgical site provides generally acceptable results. However, there are several concerns when using this type of system. For example, if a blockage occurs in the distal end of the tubing, pressure can build up in the tubing possibly causing the tubing connections to leak or even causing the tubing to rupture. Also, if the distal end of the tubing is blocked, it can cause leak back of liquid through the portion of the tubing in the peristaltic pump. Further, if the blockage is suddenly removed, a surge of liquid at an elevated pressure may be delivered to the surgical site. In addition, if there is a blockage at the fluid outlet from the surgical site, pressure can also build up inside the body cavity. These conditions may result from an accidental blockage, but also may occur when an attending physician or other medical personnel has to clamp off the end of the tubing or shut off the flow at the surgical instrument to perform an ancillary function or procedure.

Accordingly, it would be advantageous if an economical and easy-to-use system or device were available for use with the delivery of pressurized fluid to an internal surgical site to avoid problems due to blockages and pressure irregularities. Such a system may also find application in other medical and non-medical fluid delivery systems.

SUMMARY OF THE INVENTION

To address the above concerns, the present invention provides a tubing set and method for use with a system for providing pressurized fluid from a fluid source to a surgical site. The system is particularly directed for use with surgeries, such as urological, gynecological and laparoscopic surgeries, in which the surgical area is located within the body in an area accessed via a small incision or a natural orifice. The system includes a fluid source, a length of flexible tubing having one end connected to the fluid source and another end connected to a surgical instrument, and a peristaltic type pump into which a middle portion of flexible tubing is positioned so that the peristaltic type pump can pump fluid from the source to the surgical instrument by bearing on the exterior of the tubing. The improved tubing set also includes a by-pass section of tubing connected between the tubing inlet and the tubing outlet in parallel with the middle section of flexible tubing. The by-pass section provides pressure relief to the system so that pressure in the tubing will not build up distally of the location of the peristaltic pump.

DESCRIPTION OF THE PREFERRED EMBODIMENTS

Figure 1:
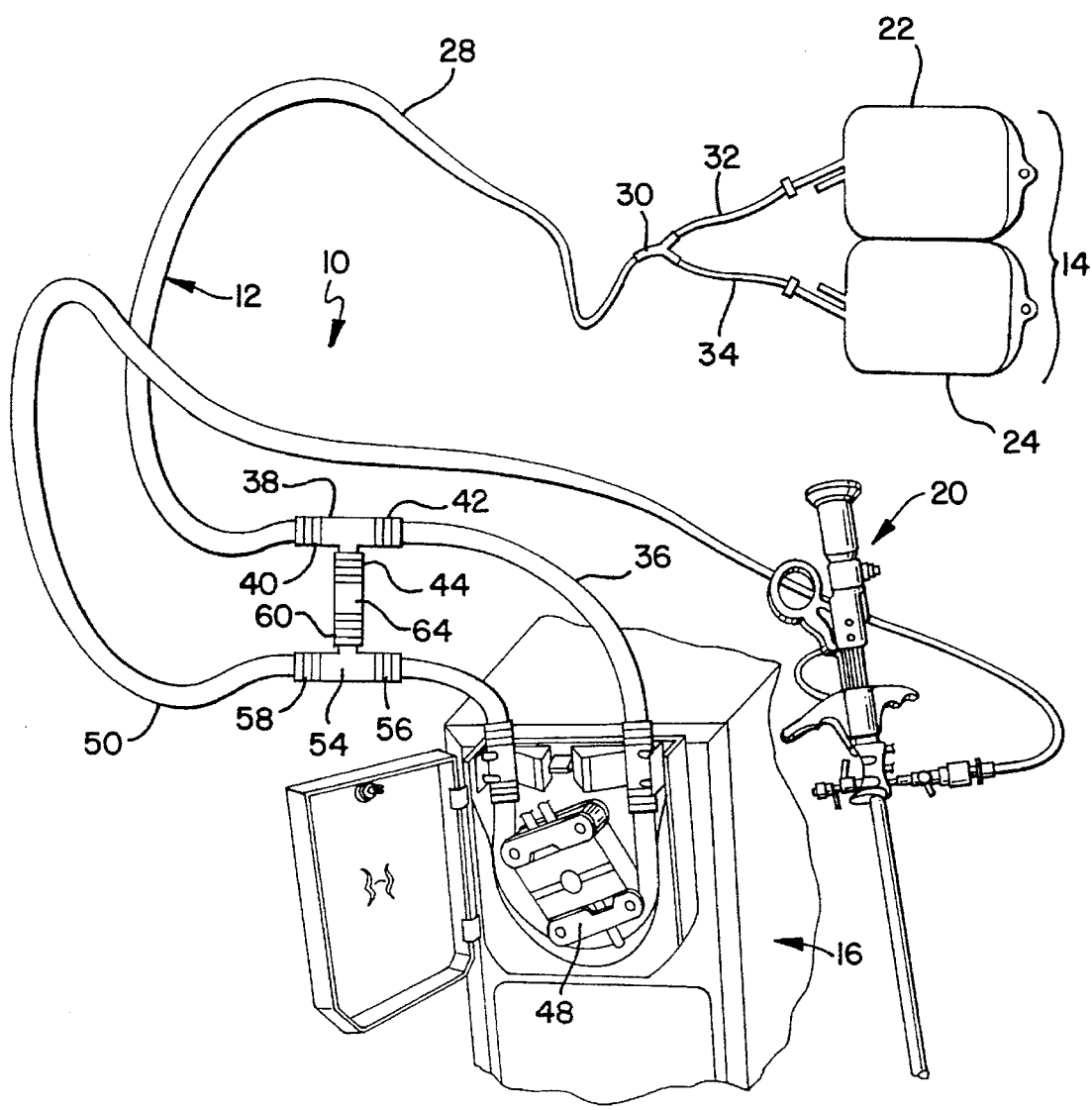
FIG. 1 is a perspective view of an irrigation system according to a first preferred embodiment of the present invention.

Referring to FIG. 1 there is shown a first preferred embodiment of the present invention. The embodiment shown in FIG. 1 is an fluid delivery system 10 that is used to provide a liquid, such as sterile water or saline, under pressure to a surgical site, and in particular to a surgical site, access to which is provided through a small surgical incision or natural orifice. Transurethral, gynecological and laparoscopic surgeries are examples of these types of surgeries.

The irrigation system 10 includes an irrigation tubing set 12 that is used in conjunction with a source of fluid 14, a pump 16, and a surgical instrument 20 to convey fluid from the source 14 to the surgical instrument 20 under pressure. The pressure is provided by the pump 16. In a preferred embodiment, the fluid source 14 may consist of one or more bags, such as bags 22 and 24, of sterile water or saline. The surgical instrument 20 may be an endoscope, a resectoscope, a laparoscope, or similar intraoperative instrument. The pump 16 may be a peristaltic or roller type pump, such as a Model Hydropump 150 by Northgate Technologies. The tubing set 12 includes a first length of tubing 28 that connects to the fluid source 14. If the fluid source 14 is comprised of more than one bag of fluid, as shown in FIG. 1, a manifold 30 may be used to interconnect the plural bags of fluid, such as bags 22 and 24, to the first section 28. Additional lengths of tubing 32 and 34 may be used to connect each of the bags 22 and 24 to the manifold 30. The sections 32 and 34 along with the manifold 30 and the first section 28 may be bonded together during the manufacturing process so that these sections are provided already assembled, or alternatively, these pieces may be provided as separate components so that they may be assembled by the medical personnel in the manner needed. In a preferred embodiment, the tubing sections 28, 32, and 34 are formed of a flexible plastic material, such as P.V.C., having a length of approximately 10 feet, an O.D. of 3/8 inches, and an I.D. of 1/4 inch. The tubing sections 32 and 34 that connect to the bags 22 and 24 may have suitable fittings for connecting to the bags in a conventional manner, such as by spiking.

Connected to the first section of tubing 28 is a second section 36. The second section 36 may be formed of a length of tubing similar to the first section 28. The second section 36 has a length sufficient for positioning in the pump 16 and in a preferred embodiment, the second section 36 has a length of approximately 10 inches. The second section 36 is connected to the first section 28 by means of a first T-fitting 38. The first T-fitting 38 may be made of a relatively hard plastic material such as polypropylene. The first T-fitting 38 has three ports 40, 42 and 44. The first section of tubing 28 connects to the first port and the second section of tubing 36 connects to the second port 42. In a preferred embodiment, the first T-fitting 38 has an O.D. of 5/16 inches and an I.D. of 1/4 inches.

The second section of tubing 36 is positioned in the pump 16 in a manner such that rollers 48 can bear along the portion of the second section of tubing 36 that is located in the pump to urge fluid in the tubing to travel from the source 14 to the tool 20. Accordingly, the material used for the second section of tubing 36 should be relatively flexible.

Connected to the second section of tubing 36 is a third section of tubing 50. The third section 50 may be formed of a length of tubing similar to the first and second sections 28 and 36. The third section 50 has a length sufficient for extending from the pump 16 to the surgical tool 20. In a preferred embodiment, the third section 50 has a length of approximately 10 feet. The third section 50 is connected to the second section 36 by means of a second T-fitting 54. The second T-fitting 54 may be similar or identical to the first T-fitting 38. The second T-fitting 54 has three ports 56, 58 and 60. The second section of tubing 36 connects to the first port 56 and the third section of tubing 50 connects to the second port 58. The connection between the third section 50 and the surgical tool 20 may use any conventional fitting.

Figure 2:
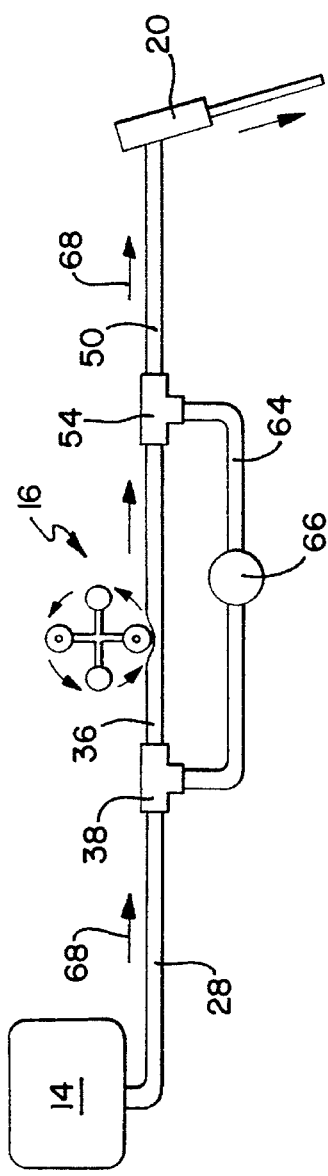
FIG. 2 is a diagram of the embodiment of the embodiment in FIG. 1 showing a first flow path.
Figure 3:
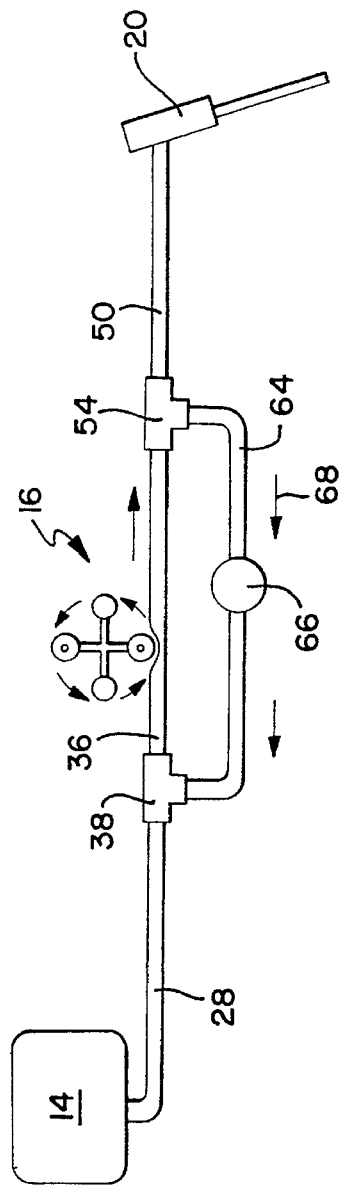
FIG. 3 is a diagram similar to FIG. 2 showing another first flow path.

A by-pass 64 connects the port 44 of the first T-fitting 38 with the port 60 of the second T-fitting 54. The by-pass 64 provides a fluid path around the pump 16 to reduce the likelihood of high pressure in the tubing 50 and/or in the patient's body. In one embodiment, the by-pass 64 provides this function by incorporating a valve 66 in a length of tubing 64 that connects the first T-fitting 38 and the second T-fitting 54. The valve is preferably a pressure valve that is normally closed, as illustrated in the diagram of FIG. 2, but opens when a pressure differential across the valve exceeds a predetermined threshold, as illustrated in FIG. 3. The fluid flow path in FIGS. 2 and 3 is shown by arrows 68.

In one embodiment, the length of tubing 64 is composed of a 3.5 inch segment of silicone tubing with an I.D. of 5/16 inches. The pressure relief valve is composed of acetal with a buna seal and stainless steel spring with an O.D. of a 3/8 inch. In a preferred embodiment, the pressure relief valve opens at a pressure of 2 pounds per square inch. In one embodiment, a suitable pressure relief valve is available from Smart Products, Inc. of San Jose, Calif.

Figure 5:
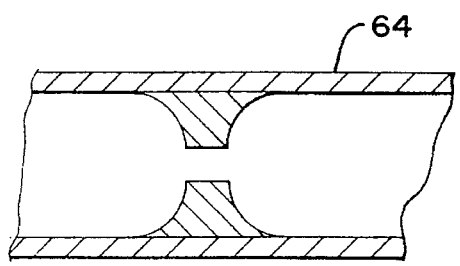
FIG. 5 is a cross section of a by-pass section of an alternative embodiment of the invention.

In an alternative embodiment, the by-pass 64 may be formed as a small orifice or restriction in a length of tubing that connects the first T-fitting 38 and the second T-fitting 54, as shown in FIG. 5. The size of the orifice or restriction is selected based upon the known size and resistance in the second section of tubing 36 and the desired operating pressure. For example, the by-pass 64 may be selected to have a relatively higher resistance to flow than the second section 38. With this alternative embodiment, there will always be some recirculating back flow in the by-pass (from the second T-fitting to the first T-fitting). If the flow downstream of the second T-fitting is not obstructed, most of the flow will go the surgical tool and into the internal body cavity. However, if there is an obstruction or if the physician turns off the flow at the tool, the amount of flow back through the by-pass will increase.

Figure 4:
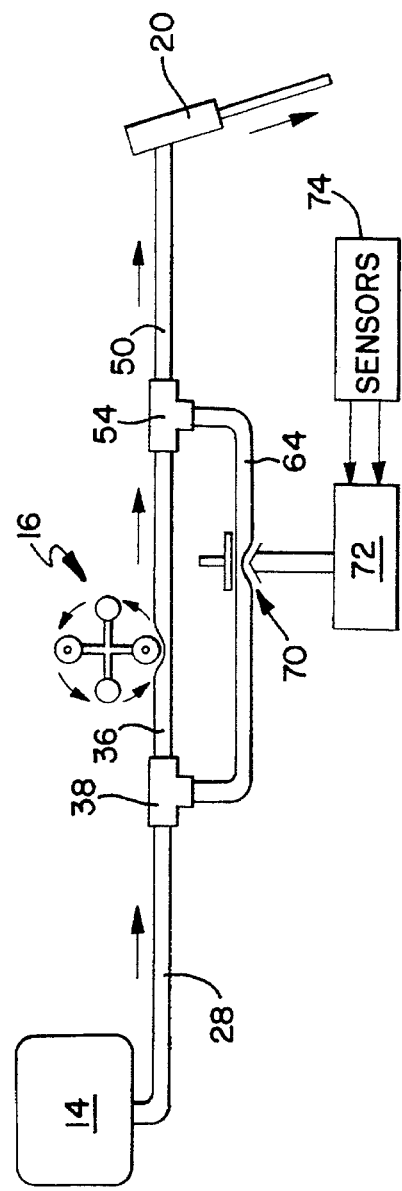
FIG. 4 is a diagram of an alternative embodiment of the embodiment of FIG. 1.

In a further embodiment, the pressure relief valve can be provided with a variable orifice to thereby provide a dynamic range of pressure values (e.g. 200–400 mm Hg). In yet a further alternative, the pressure relief valve can be operated under computer control. Referring to FIG. 4, in a computer controlled system, a pinch valve 70 located around the by-pass section 64 can regulate the flow in the by-pass by adjusting the amount by which the tubing is compressed thereby varying the resistance in the by-pass section. The amount of resistance in the by-pass section directly affects the pressure delivered to the surgical site. Accordingly, this provides for an easy way to adjust the pressure in the surgical site 64. A computer control 72 can adjust the pressure in the by-pass taking into account pressure in other parts of the system as detected by suitable located sensors 74.

The embodiments of the present invention are particularly useful when used with a positive displacement type pump, such a peristaltic pump, a roller pump, a piston or syringe pump, and so on. The present invention provides similar advantages with pumps of other types.

Although the above description pertains to a tubing set used on conjunction with the pressurized delivery of fluid to an internal surgical site, it should be understood that embodiments of the present invention could also be used with any fluid delivery to a body, such as blood, medicine, etc. Also, although the examples relate to medical applications where fluid is delivered to a patient's body, embodiments of the present invention could also be used in non-medical applications, e.g. industrial, manufacturing, etc., as well.

It is intended that the foregoing detailed description be regarded as illustrative rather than limiting and that it is understood that the following claims including all equivalents are intended to define the scope of the invention.

We claim:

1. A tubing set for use with a peristaltic pump for providing pressurized fluid from a source to a surgical instrument, comprising:

a first section of tubing having a fitting for connection to a source of fluid;

a second section of tubing being formed of a flexible material and being sized and adapted for placement in a peristaltic-type pump said second section of tubing connected to said first section of tubing;

a third section of tubing connected to said section of tubing, said third section of tubing having a fitting for connection to a surgical instrument; and a by-pass section of tubing connecting said first section of tubing and said third section of tubing, and further in which said by-pass section has a pressure relief valve that opens upon reaching a threshold pressure.

2. An improved system for providing fluid from a fluid source to a surgical site, the system including a fluid source having a fluid outlet, a surgical instrument having a fluid inlet, a roller type pump, and a length of flexible tubing having a tubing inlet connected to the outlet of the fluid source and a tubing outlet connected to the inlet of the surgical instrument, the length of tubing having at least one section between the tubing inlet and the tubing outlet formed of a compressible material, the compressible section located in said roller type pump so that fluid can be pumped from the fluid source to said surgical instrument by actuation of the pump, the improvement comprising:

a by-pass section of tubing connected between the tubing inlet and the tubing outlet in parallel with the compressible section.

3. The invention of claim 2 in which said by-pass section has a threshold resistance to fluid flow that is less than a predetermined safety limit.

4. The invention of claim 3 in which said by-pass section includes a flow restriction orifice.

5. The invention of claim 4 in which said flow restriction orifice is variable in size.

6. The invention of claim 4 in which said flow restriction orifice is fixed in size.

7. The improvement of claim 2 in which said by-pass section has a resistance to flow that is equal to or greater than a desired operating pressure at said surgical site whereby said by-pass section provides a pressure relief recirculation path for said fluid.

8. The system of claim 2 further comprising a pinch valve located external of said length of flexible tubing, and further wherein said by-pass section is positioned in said pinch valve that operates to compress said by-pass section thereby regulating the fluid flow therethrough and pressure at the tubing outlet.

9. The system of claim 8 further comprising:

a sensor operatively connected to said pinch valve.

10. The system of claim 9 further comprising: a computer responsive to said sensor and connected to and controlling said pinch valve.

11. The system of claim 8 wherein said pinch valve is adapted to compress said by-pass section of tubing over a range from fully open to fully closed.

12. An improved system for providing fluid from a fluid source to a surgical site, the system including a fluid source having a fluid outlet, a surgical instrument having a fluid inlet, a roller type pump, and a length of flexible tubing having a tubing inlet connected to the outlet of the fluid source and a tubing outlet connected to the inlet of the surgical instrument, the length of tubing having at least one section between the tubing inlet and the tubing outlet formed of a compressible material, the compressible section located in said roller type pump so that fluid can be pumped from the fluid source to said surgical instrument by actuation of the pump, the improvement comprising:

a by-pass section of tubing connected between the tubing inlet and the tubing outlet in parallel with the compressible section, and a pressure valve located in said by-pass section, said pressure valve having a predetermined pressure at which said valve opens to allow fluid to recirculate from said tubing outlet to said tubing inlet.

13. The improvement of claim 12 in which the predetermined pressure at which said pressure valve opens is in a range between approximately 200 to 400 mm of Hg.

14. A method for providing a fluid to a surgical site comprising the steps of:

attaching an outlet of a fluid source to an inlet of a tubing set;

attaching an outlet of said tubing set to an inlet of a surgical instrument;

positioning a compressible section of said tubing set in a peristaltic type pump;

positioning a by-pass section of said tubing set outside said peristaltic pump, a first end of said by-pass section connected to and communicating with said inlet of said tubing set and a second end of said by-pass section connected to and communicating with said outlet of said tubing set and in parallel with said compressible section; and operating said pump to supply fluid from said fluid source to said surgical instrument.

15. The method of claim in which said method further comprises the step of:

permitting fluid to recirculate in said by-pass section in a direction from said second end to said first end with a predetermined resistance to flow.

16. The method of claim 14 in which said method further comprises the step of:

permitting fluid to recirculate in said by-pass section in a direction from said second end to said first end when pressure at the outlet of said tubing set exceeds a predetermined threshold.

17. The method of claim 14 in which said method further comprises the step of:

permitting fluid to recirculate in said by-pass section in a direction from said second end to said first end when pressure at the outlet of said tubing set exceeds a threshold that is established by an externally provided computer control.

* * * * *

UNITED STATES PATENT AND TRADEMARK OFFICE
CERTIFICATE OF CORRECTION

PATENT NO. : 5,605,545
DATED : February 25, 1997
INVENTOR(S) : Nowosielski et al.

It is certified that error appears in the above-indentified patent and that said Letters Patent is hereby corrected as shown below:

<u>In the Claims</u>

In Claim 10, line 1, immediately after "comprising:" start a new paragraph.

In Claim 15, line 1, after "claim" insert --14--.

Signed and Sealed this

Twenty-ninth Day of September, 1998

*Attest:*

BRUCE LEHMAN

*Attesting Officer*  *Commissioner of Patents and Trademarks*